United States Patent
Margulies et al.

(10) Patent No.: US 11,103,546 B2
(45) Date of Patent: Aug. 31, 2021

(54) EDIBLE OIL COMPOSITIONS TO TREAT ORAL COMPLICATIONS AND METHODS OF USING SAME

(71) Applicant: VITA ICE THERAPEUTICS LLC, Gladwyne, PA (US)

(72) Inventors: Mark Margulies, Gladwyne, PA (US); Dennis L. Zak, Doylestown, PA (US)

(73) Assignee: VITA ICE THERAPEUTICS LLC, Gladwyne, PA (US)

( * ) Notice: Subject to any disclaimer, the term of this patent is extended or adjusted under 35 U.S.C. 154(b) by 885 days.

(21) Appl. No.: 14/609,301

(22) Filed: Jan. 29, 2015

(65) Prior Publication Data

US 2015/0209402 A1 Jul. 30, 2015

Related U.S. Application Data

(60) Provisional application No. 61/932,894, filed on Jan. 29, 2014.

(51) Int. Cl.
| | |
|---|---|
| *A61K 36/889* | (2006.01) |
| *A61K 36/00* | (2006.01) |
| *A61K 36/31* | (2006.01) |
| *A61K 36/63* | (2006.01) |
| *A61K 45/06* | (2006.01) |
| *A23D 9/00* | (2006.01) |
| *A61K 36/185* | (2006.01) |
| *A61K 36/48* | (2006.01) |
| *A61K 36/87* | (2006.01) |
| *A61K 36/28* | (2006.01) |

(52) U.S. Cl.
CPC .............. *A61K 36/889* (2013.01); *A23D 9/00* (2013.01); *A61K 36/185* (2013.01); *A61K 36/28* (2013.01); *A61K 36/31* (2013.01); *A61K 36/48* (2013.01); *A61K 36/63* (2013.01); *A61K 36/87* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2002/0168334 A1 | 11/2002 | Jacob et al. | |
| 2003/0099747 A1* | 5/2003 | Eini | A61K 47/12 426/401 |
| 2003/0236217 A1 | 12/2003 | Shalwitz et al. | |
| 2005/0222250 A1 | 10/2005 | Rezvani | |
| 2008/0011636 A1* | 1/2008 | St. John | A61K 8/19 206/449 |
| 2008/0299050 A1 | 12/2008 | Bortz et al. | |
| 2010/0178273 A1* | 7/2010 | Rottiers | A61K 31/337 424/93.2 |
| 2010/0227005 A1* | 9/2010 | Zong | A61K 31/593 424/684 |
| 2010/0278981 A1* | 11/2010 | Ervin | A23G 1/36 426/250 |
| 2012/0052128 A1* | 3/2012 | Schramm | A23D 7/005 424/498 |
| 2013/0209373 A1* | 8/2013 | Mager | A61K 31/20 424/48 |
| 2016/0228498 A1* | 8/2016 | Cunningham | A61K 9/006 |

FOREIGN PATENT DOCUMENTS

WO  2011126537  10/2011

* cited by examiner

*Primary Examiner* — Michael Barker
*Assistant Examiner* — Randall O Winston
(74) *Attorney, Agent, or Firm* — Matthew P. Frederick; Richard J. Brown; Reed Smith LLP

(57) ABSTRACT

A composition having a mixture of several different edible oils and methods of use of thereof for alleviating discomfort associated with oral complications and/or providing nutrition by administering such composition are disclosed.

20 Claims, 2 Drawing Sheets

EDIBLE OIL COMPOSITIONS TO TREAT ORAL COMPLICATIONS AND METHODS OF USING SAME

CROSS-REFERENCE TO RELATED APPLICATION

The present application claims priority to U.S. Provisional Application No. 61/932,894, filed Jan. 29, 2014 and entitled "Edible Oil Compositions to Treat Oral Complications and Methods of Using Same," which is herein incorporated by reference in its entirety.

BACKGROUND

Disorders of the mouth and throat (oral complications) adversely affect the comfort and health of a growing number of individuals in the United States and worldwide. Such disorders result in, for example, dryness or discomfort of the mouth and throat of patients. Mucositis, a disorder where there is still a pressing need for compositions and methods for relief, can occur anywhere in the body where mucous membranes are present but is most common in the gastrointestinal tract and oral cavity. The lesions can produce clinically significant pain. One problem that is typically associated with mucositis is excessive weight loss. The damage inflicted upon the oral mucosa typically makes it painful for the patient to eat. This in turn leads to malnutrition, weight loss, and susceptibility to infections. Oral mucositis refers to the inflammation and ulceration that occurs in the mouth. Besides oral mucositis, the other well-known oral complication is stomatitis. These disorders can be at least partially attributed to symptoms from chemotherapy and/or radiation therapy, HIV, anemia, Sjögren's syndrome, Dysphagia, over 400 medications, and others. Oral mucositis is a common and often debilitating side-effect of cancer treatment, e.g., chemotherapy and/or radiation therapy. Relief products for dry mouth and irritation include lozenges, sprays, gels, liquids, and cotton swabs. Although these products provide varying degrees of effectiveness, they do not deliver significant or appreciable calories or nutrition in any form. It is important to note that one of the key concerns with the aforementioned patients is not only their lack of appetite, but their inability to eat caused by oral complications. Currently-available supplements in the form of, for example, drinks, powdered mixtures, meal-replacement bars, and frozen compositions attempt to provide calories/energy for malnutrition, but do not provide prolonged and/or significant relief in the mouth.

Within the use of oral relief products there is a deeper focus on functionality than on consumer pleasure. Other than lozenges, which may have various flavors and a candy-like mouth feel, relief products like gels, sprays, and cotton swabs are not necessarily desired by the consumer. People that are experiencing a lot of oral pain can be forced into using these items, but the people that can manage the pain without these products may not choose to use them. Another concern with some of these products is their lack of dispersion. Other than liquids, which can be swished or otherwise moved around in the mouth, remedies like sprays, gels and lozenges only treat a relatively small area. Although most patients can maneuver or otherwise move lozenges around in their mouth, they do not cover a wide area because lozenges are relatively compact or small. Patients that are experiencing oral complications and struggling to consume food are usually affected in multiple areas in the mouth. Therefore, it is more difficult for such patients to pinpoint one or more specific areas with a spray or gel. Cotton swabs can be more efficient in targeting multiple areas, but they are the most uncomfortable and unnatural form of relieving oral irritation. On the contrary, liquids can be quite effective in soothing the mouth, but most of them cannot be safely swallowed or otherwise consumed due to the ingredient composition. Thus, it is more difficult to reach deeper areas in the throat with known liquids.

The supplements that are intended to deliver calories, energy, nutrition, and other related substances are typically found in the form of drinks, shakes, powdered mixtures, meal replacement bars, and some frozen compositions. These substances can include essential additives like vitamins, minerals, fatty acids, amino acids. The supplement market is important since 20% to 40% of cancer patients die from causes related to malnutrition and 80% of cancer patients develop some form of clinical malnutrition (source: National Cancer Institute). However, depending upon the severity of the oral and throat irritation, some or all of these products can be hard to swallow. Bars are rarely recommended to patients with oral complications because of their rough and dry textures. Although shakes and frozen oriented supplements can be easier to consume, they still require frequent swallowing, which can be harsh on the irritated throat.

Most patients in the categories above that are experiencing oral complications either have a lack of appetite or enough pain in the mouth that in some way limits their caloric intake. The dietary supplements described above do not provide any prolonged moisturizing sensation in the mouth. Therefore, patients with sore mouths or the inability to see food as appetizing are reluctant to use these supplements even when they are experiencing malnutrition or low levels of energy. In addition, most of the shake supplements require a relatively large serving size of at least 8 ounces, which forces the patient to swallow frequently to consume most of the product. Ideally, it would be best if the patient only had to swallow a few times to consume the recommended amount of calories.

SUMMARY

The composition of the present disclosure provides soothing relief for throat irritation and oral mucositis, for example, caused by infection, surgery, medication and the side effects of chemotherapy and radiation treatment. The composition simultaneously provides patients with oral relief and nutrition. The composition bridges the gap between oral relief products and dietary supplements by providing a good tasting, soothing product that offers relief from sore throats and mouths, while delivering substantial caloric value in a relatively small serving sizes (e.g., 1.2 ounces). In one embodiment, the composition can coat a patient's mouth and/or throat, as well as moisturize the mouth and/or throat, for less painful swallowing. The composition can be used to alleviate or eliminate dry mouth, sore throat, oral thrush, dysphagia, oral mucositis and/or malnutrition due to limited food intake.

The inventors have discovered that the compositions of the present disclosure can be used to alleviate mucositis. The term "alleviate" is used to describe a benefit observed by the inventors from the use of the compositions of the present invention, that is the compositions of the present invention reduce the discomfort and/or pain that the patient experiences from the lesions, ulcers, or sores associated with mucositis, particularly oral mucositis, or stomatitis. Aside from enhancing the patient's quality of life, the reduced discomfort and/or pain allows the patient to consume more calories (from the increased lubrication in the mouth or otherwise) and thus avoids the significant weight loss that is typically associated with mucositis. Further, maintaining a normal diet significantly reduces the potential for the patient to be placed on total parental nutrition and the disruptions in life style associated with such intensive therapy. Further, the compositions of the present invention have no known side effects, which should further benefit the patients. Thus, the invention is directed, in part, to the pallative support of mucositis such as oral mucositis or stomatitis.

In one aspect of the invention, a method of alleviating oral complications associated with cancer chemotherapy or radiation therapy in a subject (mammal or human) or patient is provided. The method involves orally administering sufficient quantity of a composition to the patient in need of such alleviation. The composition must have a mixture of several different edible oils. The composition has at least two edible oils, three edible oils, four edible oils or more as needed. Water is also added as one of the ingredients to the composition. The composition has a melting temperature in the range from 35 degrees Fahrenheit to 75 degrees Fahrenheit. The composition reduces physical discomfort and provides calories, energy or nutrition to the patient. In another aspect, a combination of packaging (a tube, a spray bottle, a cup, a pouch, or a blister pack and an edible composition within the packaging is provided. In some embodiments, the packaging includes a tube and a piston. The composition has at least two edible oils, three edible oils or four edible oils. The edible oils are any of sunflower oil, safflower oil, olive oil, coconut oil, palm oil, peanut oil, soybean oil, linseed oil, rapeseed oil, flaxseed, hempseed oil, cocoa butter, walnut oil, corn oil, grape seed oil, sesame oil, groundnut oil, medium chain triglycerides (MCT) oil, wheat germ oil, cottonseed oil, fish oil, water melon seed oil, lemon oil, orange oil, thistle oil, tomato seed oil, almond oil, perilla oil, canola oil, pistachio oil, hazelnut oil, and avocado oil and optionally water.

BRIEF DESCRIPTION OF THE DRAWINGS

The present disclosure may be better understood by reference to the description above in conjunction with the accompanying drawings. For the purpose of illustrating the present disclosure, there are shown in the drawings embodiments which are presently preferred. It should be understood, however, that the present disclosure is not limited to the precise arrangements and instrumentalities shown. In the drawings.

DETAILED DESCRIPTION OF THE INVENTION

Figure 1:
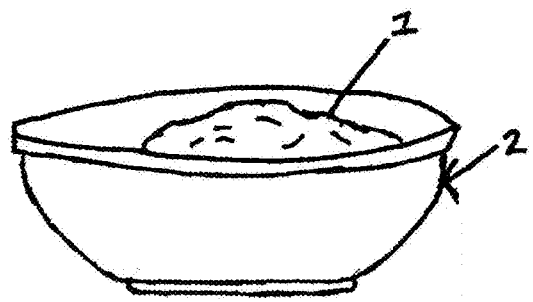
FIG. 1 is a perspective view of an exemplary form of cup packaging containing an exemplary embodiment of a frozen form according to the present disclosure.

Certain terminology is used in the following description for convenience only and is not limiting. Unless specifically set forth herein, the terms "a," "an" and "the" are not limited to one element but instead should be read as meaning "at least one." The terminology includes the words noted above, derivatives thereof and words of similar import.

The present disclosure is generally directed to a composition having a mixture of several different edible oils or fats that at least partially moisturizes the mouth, thereby treating or at least partially alleviating oral complications, and provides an appreciable amount of calories for patients. As can be gleaned from the biochemical literature, oils and fats belong to a group of biochemical substances called lipids. However, fats differ from oils in that fats are solid at room temperature. The terms "oil(s)" and "fat(s)" are used interchangeably in the present description of the invention unless otherwise indicated. Fatty acids are a class of lipids derived from hydrolysis reaction of fats and oils (triglycerides or triacylgylcerols), As already known in the art, a triglyceride or fatty acid can be saturated or unsaturated, and unsaturated fatty acids and triglycerides have lower melting points than saturated ones. Thus fats (which are solids at room temperature) are usually more saturated than oils (which are liquids at room temperature). In at least one embodiment, the composition of the present disclosure is designed to treat or alleviate oral mucositis by using a composition containing a mixture of several different edible oils or fats. The present disclosure is also generally directed to production, packaging, administering and/or consuming the composition. While the composition of the present disclosure can be particularly beneficial to human patients, pets struggling with oral and/or throat discomfort can benefit from the composition.

A purpose of the edible oil composition is to treat oral complications and/or irritations by at least partially moisturizing oral tissues, while simultaneously or concurrently providing calories for patients in need. Specific audiences of patients that are experiencing irritation in the mouth typically struggle to consume food, but are eager to treat their pain. These patients, who may also be experiencing lack of appetite, are generally not enticed to eat just for the sake of nutrients and energy. Thus, functional foods and previously available supplements are undesirable.

Edible oils are among the most abundant cooking ingredients in the world. They are extracted from plants (e.g., soybean, canola, and chili), seeds (e.g., sesame and sunflower), nuts (e.g., walnut and macadamia), and fruits (e.g., palm, olive, and coconut). Depending on oil type, they are used in baking and frying food, and for non-cooking products, such as salad dressing, margarine spreads, and dips. In addition, edible oils are used to produce non-food products such as cosmetics and as a feedstock for making biodiesel fuel. In the cosmetic industry, however, oils are only used for skin application and not intended for oral consumption.

In the food industry, it is known that dips, spreads, dressings, and cooking oils contain a large percentage of oils. However, these products are not intended to be consumed directly or alone. Dressings, dips, and spreads are always used in combination with other products, such as lettuce, crackers, or bread. Cooking oils are used specifically for cooking, and would also be undesirable for direct consumption. There are high percentages (25%-100%) of edible oils used in high calorie supplements and tube feeding applications; however, these are not intended for direct consumption. Tube Feeding of course is injected into the body and high calorie products such as BENECALORIE™ is mixed with other foods. These items would not be at all desirable to eat alone. In contrast, in at least some embodiments of the present disclosure, the edible oil composition is intended to be consumed directly and not in combination with other products.

One aspect of the present disclosure is directed to a method of treating an oral complication by orally administering or consuming a composition having a mixture of several different edible oils. The composition can include as many as two, three, four, five or more edible oils. Examples of suitable edible oils for the embodiments of the present disclosure include, but are not limited to, sunflower oil (including high oleic sunflower oil), safflower oil (including high oleic safflower oil), olive oil, coconut oil, palm oil, peanut oil, soybean oil, linseed oil, rapeseed oil, flaxseed oil, hempseed oil, cocoa butter, walnut oil, corn oil, grape seed oil, sesame oil, groundnut oil, wheat germ oil, cottonseed oil, fish oil, watermelon seed oil, lemon oil, orange oil, thistle oil, tomato seed oil, almond oil, perilla oil, canola oil, pistachio oil, hazelnut oil, avocado oil, and the like, and mixtures or fractions thereof.

In one embodiment of the present disclosure, the composition can include at least two edible oils. For example, one embodiment contains a mixture of only coconut oil and canola oil. However, in another embodiment of the present disclosure, the composition can include three edible oils, such as olive oil, coconut oil, and canola oil. In other embodiments of the present disclosure, different combinations of edible oils may exist.

Figure 3:
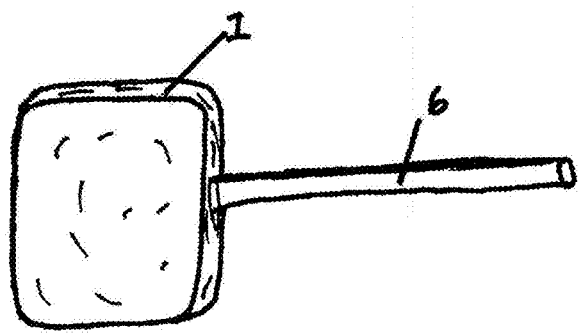
FIG. 3 is a perspective view of an exemplary embodiment of the frozen form according to the present disclosure attached to a stick that the patient can use to hold and/or administer the frozen product.
Figure 4:
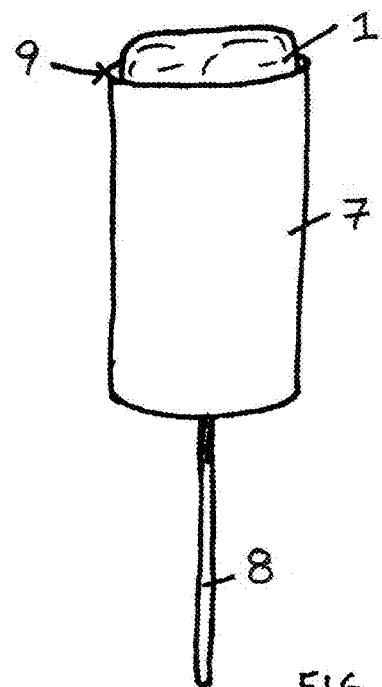
FIG. 4 is a perspective view of an exemplary embodiment of at least a partially frozen form according to the present disclosure in a tube packaging, wherein a stick can be pushed upwardly and/or outwardly so that the product becomes at least partially accessible at a top of the tube for consumption and/or administration.

It is also desirable to produce an edible oil composition or mixture in at least a partially or completely frozen form because it may be the case that the most effective application is when the composition is in a frozen state. For example, as shown in FIG. 3, the edible oil composition, generally designated 1, can be adhered to or at least partially frozen around or on an end of a stick 6. Similarly, as shown in FIG. 4, the at least partially frozen composition 1 can be at least partially contained within a tube 7 and movable by a rod or piston 8, whereby the piston can expose at least a portion of the composition 1 for consumption at one end 9 of the tube 7. In such an embodiment, the composition 1 can include a mixture of several different edible oils and water. Upon freezing or refrigeration of the edible oil composition 1, the volume, depth and/or width of the composition 1 will be greater than that of pure liquid oil composition. This can allow the patient to more easily move the item or at least a portion of the composition 1 around in his or her mouth or at least partially chew it before swallowing, or to simply allow the item to dissolve into the mouth while effectively moisturizing at least some oral tissues, and at least portions of the lips and/or throat.

In some embodiments, a mixture of several different edible oils can be some or all of extra virgin, virgin, unrefined, or refined coconut oil or olive oil. Olive oil and coconut oil have widely different melting points or temperatures (approximately 21 degrees Fahrenheit and 76 degrees Fahrenheit, respectively) and both have trending health benefits in the marketplace. These contrasting temperatures allow for mixtures of the oils to have properties that will help with the mouth feel of the composition of the present disclosure by providing a frozen embodiment that is not too hard to chew and swallow. It is important to achieve the optimal melting temperature to achieve a smooth and desirable texture for these patients.

A combination of oils and water according to the present invention creates the most desirable texture for direct patient consumption. Through the use of canola oil, olive oil, coconut oil and others (listed elsewhere herein) and with the addition of water as well one can achieve a soothing and extremely smooth product. When one of the ingredients is used in excess the throat may burn, the composition may cause choking due to slow and thick movement toward the esophagus, the texture may be hard or waxy, and/or may be too oily in the mouth. It is vital to use at least two oils to achieve the desirable melting temperature, which will equate to having a smooth product. A subject's mouth with oral complications can be extremely sensitive, so it is important to give them something that will not provide further irritation, coughing, or nausea (e.g., due to a product being too oily). Some of patients (exposed to chemo or radiotherapeutic agents) may already experience nausea, so a product that is too oily may further enhance this symptom. The melting temperature range can be in between 35 degrees Fahrenheit and 75 degrees Fahrenheit when all of the oils are combined with the water as well. It is preferred to achieve a frozen solid state when the product is placed in the freezer. The product may be consumed as a liquid, but preferably it is stored and served frozen. The product can be formulated to achieve high levels of smoothness and creaminess at frozen temperatures except for the spray bottle embodiment. Other oils besides canola oil, olive oil, and coconut oil can be used provided, however, that at least one of the oils itself must have a melting point or temperature of at least 75 degree Fahrenheit (such as coconut oil and palm oil). These will provide the solid structure for the base of the product. When other oils are used in combination with these more saturated fats, then the melting point or temperature will drop based upon the interaction between these various oils used (i.e. coconut oil with sunflower oil and soybean oil). The melting point or temperature needs to be controlled for an adequate mouth-feel and delivery in the mouth and throat for subjects with oral complications. Oils when combined with each other and water (at the appropriate ranges) will create smooth mouthfeel, desirable thickness for proper swallowing, neutral flavor, and an adequate level of coldness upon consumption (oils formulated together without water do not provide the cold feeling to the same extent as those with water do when refrigerated or frozen).

At least some embodiments of the present disclosure utilize high fat concentrations, which make them unique to the frozen or cold food category. For example, ice cream is typically packaged in a barrier container and can contain a minimum of 10% fat and around a maximum of 16% fat. In the prior art, significant attention has been directed toward reducing the fat and cholesterol contents within these items. The composition of the present invention, however, can include a high percentage of fat content, such as approximately 60-100% fat content by weight (e.g., grams). The high fat concentration in at least some of the embodiments of the composition of the present disclosure exceeds the maximum amount found in ice cream products. Consuming fats directly at this level are not known in the prior art to be desirable for direct consumption, except for the dietary supplement, which will be discussed in a later specification.

In the frozen or cold food category, oils are also used in ice cream coatings, formerly known as compound coatings. Compound coatings use a percentage of vegetable oils ranging from 28% to 70% fat, which is greater than the percentage of fat found in ice cream. It is known that above 65% fat content is considered extremely high for a compound coating. Compound coatings, however, are not consumed alone. The compound coatings act as the barrier to protect the interior of ice cream and other soft serve frozen edible novelty products, to maintain their (e.g., ice cream) character as a cohesive and solid mass when exposed to a temperature above ice cream or frozen edible novelty product's melting point, to resist drippage as the ice cream or other soft serve frozen edible novelty product melts, and to be able to be conveniently served and consumed at a higher temperature than those without the compound coatings, and at times to allow the consumer to grasp the item with their hands.

Therefore, since compound coatings are exposed directly to air, and ambient temperature often above ice cream or other soft serve frozen edible novelty product's melting point and to the consumer's hands, they need to be delivered at a melting point of about 75 degrees Fahrenheit to 105 degrees Fahrenheit. This melting temperature range can create a harder texture, thereby creating less overall lubrication in the consumer or patient's mouth. However, at least some of the frozen or cold embodiments of the present disclosure can have a melting point that is substantially lower than 75 degrees Fahrenheit. In one embodiment, the melting temperature range will be from 35 degrees to 75 degrees Fahrenheit for desirable mouthfeel and thickness for swallowing. Because the composition of the present disclosure is produced with different packaging (surrounding package barriers) then the way in which compound coatings are typically formed, this allows for a significant decrease in the melting temperature below 75 degrees Fahrenheit and an increase in the percentage of the edible oils (e.g., in excess of 60%), thus providing a more intense and/or desirable moisturizing sensation in the mouth without the undesirable effects of a messy, soft product. In one embodiment, the percentage of edible oils will be composed of 70%-95% oil.

Packaging can be extremely important in how consumers use a product. In the dietary supplement industry, products such as coconut oil, fish oil, and medium chain triglycerides (MCT) oil, are used directly for a variety of different health benefits. Typically the consumer can buy these items in a few different packaging forms. The oils can be packaged in a glass container, in capsule form, or in a plastic container rather than glass. All of these forms are sold and known to be used at room temperature.

Oils packaged directly in glass containers and also in capsules are not conducive for freezing, because the glass would break and the capsule adds no extra benefit from being frozen. Plastic containers are used for highly saturated fats such as coconut oil, which could be placed in the freezer; however, due to the increased melting point of highly saturated fats, the freezer will create disappointment for the consumer as it will be difficult to then scoop or use the product after being frozen. Other oils that are low in saturated fats and thus more freezer compatible are also packaged in plastic containers. However, these containers and bottles are only conducive for pouring and not scooping, which makes sense because unsaturated fats have lower melting points and are usually liquid at room temperature. Therefore, freezing the item would make it extremely hard for the consumer to use the oil as the top of the bottle or container has a very small opening. Thus, packaging in the dietary supplement industry does not make it conducive or beneficial for freezing. In addition, although these supplements are taken without the addition of other foods, they are not created to be desirable for direct consumption. The packaging of at least some embodiments of the present disclosure contains the composition or edible oils in a barrier, which allows for such a high concentration of oils with a lower melting temperature than what is typically found in the comparable compound coating range.

At least one difference between the frozen or cold embodiment of the present disclosure and other frozen products in the marketplace is the functionality of the present disclosure (e.g., the targeted prolonged moisturizing sensation). Most conventional frozen product manufacturers are attempting to decrease calories and fat. While in contrast, it is important for the composition of the present disclosure to deliver calories in the form of moisturizing edible oils because specific patient groups are struggling from malnutrition due to the lack of ability to swallow and consume foods.

Figure 5:
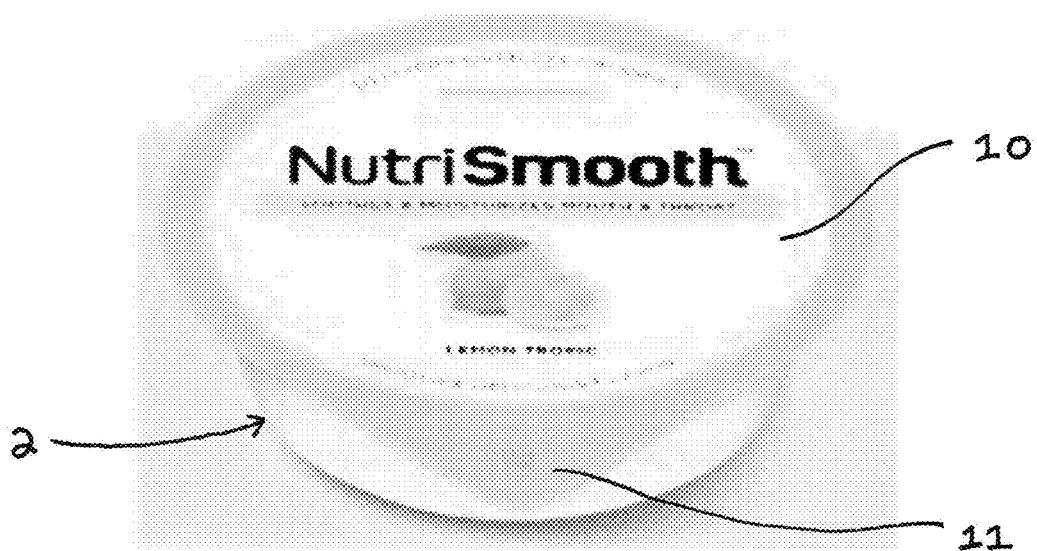
FIG. 5 is a perspective view of another exemplary form of cup packaging containing an exemplary embodiment of a frozen form according to the present disclosure, wherein the frozen form is concealed beneath a removable cover or top.

For example, as shown in FIG. 5, a removable lid 10 can be attached to a cup or bowl 2 containing the edible composition (not shown). A portion of the lid 10, such as a flap 11, can extend significantly beyond the outer perimeter of the cup 2 than the remaining portions of the lid 10, so as to aid in separation or removal or the lid 10 from the cup 2. The cup 2 can include a wide top (70 mm to 100 mm in diameter) or opening to enable spoon insertion to enable to patient or a healthcare working to scoop out the composition within the cup 2.

In other embodiments of the present disclosure, packaging can be essential for success in the deliverance of the edible oil composition to the patients. The packaging can allow the consumer to grasp the edible oils more conveniently at ambient temperatures without the drippage and loss of cohesiveness. Drippage or loss of cohesiveness can result in soiled hands, clothing, and the like if care is not taken when these edible oils are eaten from the packaging held by their hands. It is also possible to provide a packaging design to have the ability to deliver the item to a patient who cannot actually grasp it on his own. For example, the composition can be packaged in different forms and materials.

In some embodiments of the present disclosure, the composition can be packaged in frozen, refrigerated, or room temperature form. The product is formulated for frozen consumption and to achieve best creamy, smooth texture when placed in freezer. In some embodiments of the present disclosure, the composition can be packaged in a tube 7 (see FIG. 4), provided in a cup or bowl 2 (see FIG. 1) and accessible by a spoon, for example. In some embodiments of the present disclosure, the composition can be packaged in a bag, a blister pack, surrounded by a film, or in a pouch application. Suitable examples of the materials of the packaging include, but are not limited to, paper or plastic forms. In another embodiment, the composition is sealed in the package. The packaging can be a one, two, three, or four sided, sealed and flexible application.

In a further embodiment, the packaging can be portion controlled, yet still provide patients with a sufficient amount of calories in smaller bites. Suitable patients for the composition of the present disclosure are those who are struggling to eat and do not want to consume large amounts of a supplement or food, especially if they are having difficulty swallowing. Therefore, the composition can be in portioned packaging to limit the amount of movement in the mouth and swallowing required due to the decreased amount of portioned product that they are ingesting. Specific oils, like coconut oil and olive oil, can be preferred in such an embodiment. Edible oils can be preferred due to their desirable melting points, interaction with other oils, health benefits, and allergen impact, for example.

Patients that want to consume a product with varying degrees of thickness for swallowing purposes can use a tube 7 (see FIG. 4), a cup or bowl 2 (see FIG. 1), film, bag, a one, two, three, or four sided sealed package, and/or pouch containing various degrees of formula thickness. Specific thickeners can be added to the formulation containing saturated and unsaturated fats. Such an embodiment can be consumed at room temperature, refrigeration temperature, or at a frozen temperature. This specific embodiment can be designed for patients who are looking for calories, lubrication, and an aid in swallowing (e.g., dysphagia patients). Such a composition will still be lubricating, but may be a bit thicker and viscous than certain embodiments described herein.

In one embodiment, a frozen composition including a mixture of several different edible oils is packaged into a one, two, three, or four sided sealed plastic bag. In another embodiment, the package can be produced and shipped at room temperature and then frozen upon arrival at the final destination.

In another embodiment, as described above, the packaging of the edible product or composition 1 can allow the product to be consumed by a patient holding a stick 6 or piston 8 (see FIGS. 3 and 4) attached to the at least frozen edible oil composition 1. In other embodiments, the composition can be found without a stick and can be produced in both bite size (e.g., individually wrapped) and larger shapes (e.g., the size of an ice cream bar). In a further embodiment, the stick, bite size and bar form can be packaged in a wrapped seal, bag, or cup. In a further embodiment, as described above and shown in FIG. 4, the packaging can include a cylindrical tube 7 and stick mechanism or piston 8 for the patient to consume the composition 1 by pushing on at least a portion of the piston 8, thereby causing the composition 1 to at least partially come out of the tube 7 at one end 9 thereof. Ultimately, the composition 1 of such an embodiment can be less moisturizing to a patient's mouth, because the melting temperature of the composition would need to be higher in order to provide a thickness that could support the structure of the composition. Similar to the compound coatings addressed above, the melting temperature would need to be higher and, thus, such an embodiment can provide overall less lubrication. For example, coconut oil or other high melting temperature oils may be included in the composition to texturize and thicken the product. In contrast to an edible compound coating, this product or composition can have more volume and mouth-feel benefits. Thus, the ability to grasp the product without a drippage or other mess would increase significantly and the patient would be more satisfied.

An alternative embodiment can include the composition in a polymeric, elongated pouch, where one end of the pouch can be opened (e.g., cut with scissors) to expose and thereby consume at least some of the composition. At least some of the composition can be removed from the pouch by pushing or compressing (or pull) a portion of the pouch away from or toward the opening.

Figure 2:
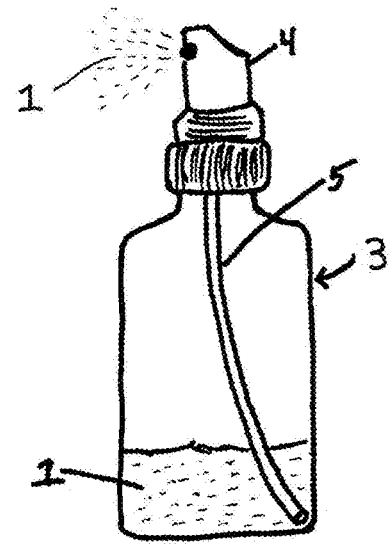
FIG. 2 is a perspective view of an exemplary form of spray-bottle packaging, which includes a storage area containing an exemplary embodiment of a liquid form according to the present disclosure.

Referring to FIG. 2, patients that want convenience and fewer, yet significant, calories from a composition for dry mouth relief can use a spray bottle packaging, generally designated 3, which allows for delivery or administration of the composition 1 in the form of liquid in a mist or spray. In this packaging application, the blend of the composition 1 can contain one or more edible oils, excluding highly saturated fats, such as coconut oil due to the thickness of the oil and the potential for clogs due to such fats in the sprayer 4. For example, one embodiment can include a composition with a mixture of olive oil and canola oil. Oils that are in the liquid state at room temperature may be used in this packaging. The composition 1 may be cooled, but it is not recommended to be placed in the freezer as this may thicken/freeze the oils and potentially cause the sprayer 4 or inner tube or straw 5 to clog. Water can also be added to the composition for impact on texture and efficacy of spray. This alternative of spray bottle packaging can be recommended for those who want lubrication, but want to control caloric intake (e.g., Sjögren's syndrome patients).

In one embodiment, the composition can be formed of 0.01-49% olive oil, 10-85% coconut oil, and 15-90% canola oil. The above percentages create a desirable mouth feel, taste, and sensation in the mouth and throat of a patient. The composition can have a melting temperature of oil formation in the range of 0-75 degrees Fahrenheit. More specifically, the composition can include a unique blend of plant oils (e.g., canola oil, coconut oil, olive oil), purified water, cane sugar, natural lemon and tropical flavors. In another embodiment of the present disclosure, such as with use of the spray bottle 3 (see FIG. 2), the composition can include highly unsaturated fats and comprise 25-100% canola oil, 25-100% olive oil, and 0.01-75% water ($H_2O$). Stated differently, the composition can include 25-100% oil and 0.01-75% water. The melting temperature range for the composition of the spray bottle application may be −15-75 degrees Fahrenheit. Preferably, in the spray bottle application, the melting point of a mixture of several different edible oils is from −15 to 35 degrees Fahrenheit due to the usage of highly unsaturated fats which have inherently lower melting temperatures.

Figure 6:
FIG. 6 is an exemplary nutrition label for one or more of the packaging containing the exemplary forms described herein.

As understood by those skilled in the art, the composition of the present disclosure can provide essential amounts of calories to the patients. Therefore, the present disclosure serves both functional and health related benefits by delivering calories and providing a soothing benefit to the mouth, lips, and throat. In order to gain benefits, the patient can consume sufficient quantities of a composition herein. For example, the exact quantity required to alleviate a disorder (mucositis or stomatitis) will vary depending upon the severity of the patient's disorder, the chemotherapy and/or radiation regimen that the patient is exposed to, inflammatory condition of oral tissue, including mucosa, the patients age, the presence of other diseases besides cancer, etc. The composition can be consumed in one sitting, but it is preferred if the patient gradually consumes the composition on a periodic basis throughout the day (i.e., 2-4 times especially during their eating periods). The composition can also help the patient to further consume additional foods by coating and lubricating their irritated mouth. FIG. 6 shows an exemplary nutrition label, generally designated 12, for the composition according to at least one embodiment of the present disclosure. The edible composition can provide approximately 235 calories per serving, which is considered to be in the range defining an appreciable amount of calories for a patient.

In some embodiments, supplementary ingredients can be added to the composition, such as for added health and functionality purposes. In one embodiment, the composition can include at least one or two or more vitamins. The vitamin can be selected from the group consisting of Vitamin A, Vitamin B, Vitamin C, Vitamin D, Vitamin E, Vitamin K, and any combinations thereof. In the same or another embodiment, the composition can include at least one mineral (e.g., table salt) and/or at least one mineral element in a suitable form (e.g., salt, compound, chelated, etc.). Examples of minerals include, but are not limited to, calcium, phosphorus, potassium, sodium, chloride, magnesium, sulfur, iron, iodine, zinc, chromium, selenium, fluoride, molybdenum, copper, manganese, and any combinations thereof. In another embodiment, the composition can include alternative or additional nutritional elements, such as protein, fiber, and amino acids.

In addition to delivering nutrition and calories, the functionality of the oral component of the present disclosure is important. The composition can include at least one desirable melting temperature point, which will provide a moisturizing sensation in the mouth, lips, and in the throat. In some embodiments, the composition will also coat at least a portion of the mouth and allow for consumption of other compositions. In other embodiments, ingredients can be used to complement the oral component of the invention, such as xylitol, menthol, eucalyptus oil, lemon, mint, peppermint, spearmint, essential oils, aloe vera, tea tree, malic acid, citric acid, and tartaric acid. In another embodiment, demulcents like pectin, honey, glycerin, and syrup can be used to help with throat irritation. Additionally, synthetic demulcents, such as methyl cellulose, propylene glycol, and glycerin can be used for some audiences.

It can also be beneficial to add other ingredients to stabilize the product or composition, and also add specific functionality. In some embodiments, an aqueous base can be added with edible oils for functionality, texture, and health purposes. An aqueous base can be helpful to decrease the amount of saturated fats in compositions using certain edible oils. In other embodiments, the other ingredients can include sugar, lecithin, gums, emulsifiers, thickeners, flavoring agents, coloring agents, and the like. Compositions of the present invention will also typically include a flavor to enhance its palatability, especially in a pediatric population. Useful flavorings include, but are not limited to, lemon, cherry, orange, grape, fruit punch, bubble gum, apple, raspberry and strawberry. In some embodiments, cream, milk, fruit and vegetables in the form of juice or purees, or water can be blended with the edible oil composition, which can contribute to or enhance the satisfying mouth feel of the composition. Flavors of the composition may be directly linked to creaminess, which can both enhance desirability.

An aqueous base in the composition will hydrate the consumer's throat as the edible oils are being ingested and swallowed. An aqueous base will increase the movement of the formulation and thus alleviate coughing due to the slow movements of the oils. It may be important to use an efficient amount of water to compensate for the texture, flavor, melting temperature, lubrication to the mouth and throat, as well as overall desirability. In at least one embodiment of the present disclosure, water may be added at the following percentages: 0.1%-40% by weight (e.g., grams). An emulsion may be necessary in such an embodiment. For example, xanthan gum is known to emulsify salad dressings, which contain water and oil. The emulsion at the proper percentage will only bind the product and allow for a more desirable texture during the freezing process.

In some embodiments, the composition can include a therapeutic agent. The terms "therapeutic agent" and "drug" and "agent" are used interchangeably herein to refer to a compound that, when present in a therapeutically effective amount, upon exposure to a site of action, produces a therapeutic effect, and whose site of action is located or whose effect will be exerted on the surface or inside target cells. In some embodiments, the therapeutic agent may be pertinent for the irritation of the mouth or for infection. Such agents can include antibiotic, analgesic, antipyretic, anesthetic, and antifungal agents. In other embodiments, the agent is an antibiotic to kill bacteria around the sore, an antihistamine or local anesthetic to reduce pain and discomfort, an antifungal to reduce fungal growth, a corticosteroid to treat inflammation, or an antacid to enhance coating of the other ingredients inside the mouth. Additionally or alternatively, the composition can include one or more of lecithins, gums, emulsifiers, thickeners, flavoring agents, coloring agents and fruits for stability and desirability in texture, perception and/or flavor.

In use, the composition can be consumed or applied before, during and/or after a meal, or anytime the patient's mouth and/or throat are sore or irritated. Consuming or applying the composition at mealtime will help to coat and soothe the mouth in order to help the patient feel better and allow other foods to be more easily consumed. For the frozen embodiment of the composition 1, a spoon can be used to shave the composition from the cup 2, for example. The shaved composition pieces can be ingested or applied in relatively small amounts to effectuate relief from sore mouth and/or throat. The composition 1 is shelf-stable and does not require refrigeration. However, the patient may desire that the composition 1 is frozen before serving or consumption.

The present disclosure also relates to processes to manufacture the composition described in detail above. The composition may be prepared or produced in a warm, cool, or frozen environment. In one embodiment, the composition may be filled and sealed through a liquid dispenser. In another embodiment, the edible oil composition may be produced in a frozen production plant. The composition may be produced in a bite size oriented shape, as well as in a longer shape. Both large and small shapes may be produced with a stick for the consumer to grasp upon consumption. In a frozen production plant, the item may be extruded and molded.

The following examples are being disclosed in order to in order to illustrate the invention. The examples should not be construed as limiting the invention in any manner.

EXAMPLE 1

The following is a representative example of a composition containing a mixture of several different edible oils or fats and water so that at least partially moisturizes the mouth, thereby fully or at least partially alleviating discomfort associated with oral complications, and also provides an appreciable amount of calories for patients.

| Ingredients | % (w/w) |
| --- | --- |
| Canola oil | 42.1% |
| Coconut oil | 25.67% |
| Olive oil | 10.26% |
| Water | 12.83% |
| Sugar | 7.7% |
| Xanthan gum | 0.25% |
| Flavoring (lemon and tropical) | 1.2% |

The above exemplary composition was prepared as follows: All of the oils were mixed together. Each oil may be refined, bleached and deodorized. Separately, to the entire amount of xanthan gum, cane sugar (e.g., in powder form) was added at a 1 to 5 ratio. Then, water (e.g., purified) was added to the blend of xanthan gum and sugar, and mixed for one minute. To this, the oil mixture and remaining sugar were added. This blend was then mixed for 10 minutes in a blender. This blended mixture was taken and poured out into small portion cups. Portion cups were cooled down for 20 minutes. They were then placed in the freezer to mold into their shape.

EXAMPLE 2

The purpose of this example is to examine formulation on human subjects with oral complications.

Subject 1 (a 63-year-old female head and neck cancer patient) was given the composition according to Example 1. This subject stated that "I have gone through 17 years of swallowing discomfort and have tried everything. This product is very easy to swallow and the lubrication lasted over an hour in my mouth. This product is more effective than biotene."

Subject 2 (a 65-year-old female breast cancer patient) was given the composition according to Example 1. The subject stated that "I suffer from oral thrush and also experience an odd salty taste in my mouth. I like the way this product feels on my tongue. It's a soft, soothing feeling."

Subject 3 (a 55-year-old female non Hodgkins Lymphoma patient) was given the composition according to Example 1. This subject stated that "[t]he initial lemon flavor was great. Anything that can be consumed with little effort, has a good initial taste, has the nutrients, and doesn't require a 'big glass' full will be welcomed by chemo patients."

Subject 4 (a 52-year-old Former Breast Cancer Patient) was given the composition according to Example 1. This subject stated that "[s]wallowing smoothies and milkshakes hurt my throat when I was undergoing treatment. This product is perfect for sliding right down"

Subject 5 (former Aplastic Anemia-Stem Cell Transplant Patient) was given the composition according to Example 1. This subject stated "[m]y chemotherapy treatment dosage was the equivalent of a 6 month breast cancer patient, but all taken in one week. I tried Ensure, but it wouldn't go down, it was too liquidy. I loved popsicles and cold, soothing items through my treatments."

EXAMPLE 3

The purpose of this example is to examine patient (human subject with oral complication) response to a composition containing a mixture of several different edible oils or fats (with 100% oil product and flavoring) with no water (see the chart below).

| Ingredients | % (w/w) |
| --- | --- |
| Canola oil | 42.3% |
| Coconut oil | 28.0% |
| Olive oil | 23.0% |
| Sugar | 4.8% |
| Flavoring (lemon and tropical) | 1.9% |

Subject 6 (a 55-year-old breast cancer patient) was given the composition according to Example 3. This subject stated that "too oily, not pleasant texture. Would not consume if nauseous. Would feel nauseous a day or two after treatment."

Subject 7 (a 70-year-old female breast cancer patient) was given the composition according to Example 3. The subject stated that "like the ease in getting calories." She noticed a few coughs after consuming the product.

Subject 8 (a patient experiencing oral thrush) was given the composition according to Example 3. This subject stated that "like the way it feels, but seems to be Vaseline oriented."

Subject 9 (a 55-year-old breast cancer patient): This subject drank olive oil three times a day before meals during treatments. It was extremely difficult for her to drink down. Burning and coughing occurred. This subject was given the composition according to Example 3. Subject 5 (former Aplastic Anemia-Stem Cell Transplant Patient) was given the composition according to Example 3. This subject liked the texture of the product; expected it to be colder.

The features and advantages of the present disclosure will be readily apparent to those skilled in the art. While numerous changes may be made by those skilled in the art, such changes are within the spirit of the invention. For example, one or more components of any embodiment of the composition may be removed therefrom or added to another embodiment described herein.

We claim:

1. A method of alleviating discomfort of oral complications associated with cancer chemotherapy or radiation therapy in a patient, the method comprising:
    orally administering sufficient quantity of a composition to the patient in need thereof, the composition consisting essentially of 1%-40% by weight of water and a mixture of at least two edible oils;
    wherein the composition consists essentially of at least 60% oil or fat,
    wherein the composition has a melting temperature in the range from 35 degrees Fahrenheit to 75 degrees Fahrenheit,
    wherein at least one edible oil in the composition has a melting temperature above 75 degrees Fahrenheit selected from the group consisting of coconut oil and palm oil and at least one edible oil in the edible composition has a melting temperature below 35 degrees Fahrenheit selected from the group consisting of canola oil, olive oil, sunflower oil and soybean oil;
    an emulsifier; and
    optionally at least one component selected from the group consisting of vitamins, minerals, therapeutic agents, additional nutritional elements, demulcents, sugar, lecithin, thickeners, flavoring agents, and coloring agents;
    wherein said composition is formulated to alleviate discomfort of oral complications associated with cancer chemotherapy or radiation therapy in a patient.

2. The method of claim 1, wherein the oral complications are oral mucositis or stomatitis.

3. The method of claim 1, further comprising:
    at least partially freezing the composition prior to oral administration to at least temporarily relive oral pain.

4. The method of claim 1, further comprising:
    enclosing the composition in a package prior to administering to the patient, the package being selected from the group consisting of a tube, a spray bottle, a bag, a cup, a pouch, film, and a blister pack.

5. The method of claim 4, wherein said package is a spray bottle and wherein said composition is orally administered to the patient through the spray bottle.

6. The method of claim 1, wherein the composition includes at least one vitamin, the at least one vitamin being selected from the group consisting of Vitamin A, Vitamin B, Vitamin C, Vitamin D, Vitamin E, Vitamin K and any combinations thereof.

7. The method of claim 1, wherein the composition includes:
    at least one therapeutic agent; and
    at least one mineral, the at least one mineral being selected from the group consisting of calcium, phosphorous, potassium, sodium, chloride, magnesium, sulfur, iron, iodine, zinc, chromium, selenium, fluoride, molybdenum, copper, manganese and any combinations thereof.

8. An edible composition consisting of:
1%-40% by weight of water, and
a mixture of at least two edible oils;
wherein the edible composition consists essentially of at least 60% oil or fat,
wherein said edible composition has a melting temperature in the range of from 35 degrees Fahrenheit to 75 degrees Fahrenheit,
wherein at least one edible oil in the edible composition has a melting temperature above 75 degrees Fahrenheit selected from the group consisting of coconut oil and palm oil and at least one edible oil in the edible composition has a melting temperature below 35 degrees Fahrenheit selected from the group consisting of canola oil, olive oil, sunflower oil and soybean oil;
an emulsifier; and
optionally at least one component selected from the group consisting of vitamins, minerals, therapeutic agents, additional nutritional elements, demulcents, sugar, lecithin, thickeners, flavoring agents, and coloring agents;
wherein said edible composition is formulated to alleviate discomfort of oral complications associated with cancer chemotherapy or radiation therapy in a patient.

9. The composition of claim 8, wherein the mixture of at least two edible oils consists of three edible oils.

10. The composition of claim 9, wherein the mixture of at least two edible oils consists of canola oil, coconut oil and olive oil.

11. The composition of claim 8 including:
at least one vitamin, wherein the at least one vitamin is selected from the group consisting of Vitamin A, Vitamin B, Vitamin C, Vitamin D, Vitamin E, Vitamin K and any combinations thereof;
at least one mineral, wherein the at least one mineral is selected from the group consisting of calcium, phosphorous, potassium, sodium, chloride, magnesium, sulfur, iron, iodine, zinc, chromium, selenium, fluoride, molybdenum, copper, manganese and any combinations thereof; and
at least one therapeutic agent.

12. The composition of claim 8, wherein the composition has a melting point substantially lower than 75 degrees Fahrenheit.

13. The composition of claim 8, wherein the composition is at least partially frozen.

14. A combination comprising:
a package selected from the group consisting of a tube, a spray bottle, a cup, a pouch, or a blister pack; and
an edible composition within the package, the edible composition consisting of 1%-40% by weight of water and at least two edible oils;
wherein the edible composition comprises at least 60% oil or fat,
wherein said edible composition has a melting temperature in the range of from 35 degrees Fahrenheit to 75 degrees Fahrenheit,
wherein at least one edible oil in the edible composition has a melting temperature above 75 degrees Fahrenheit selected from the group consisting of coconut oil and palm oil and at least one edible oil in the edible composition has a melting temperature below 35 degrees Fahrenheit selected from the group consisting of canola oil, olive oil, sunflower oil and soybean oil;
an emulsifier; and
optionally at least one component selected from the group consisting of vitamins, minerals, therapeutic agents, additional nutritional elements, demulcents, sugar, lecithin, thickeners, flavouring agents, and coloring agents;
wherein said edible composition is formulated to alleviate discomfort of oral complications associated with cancer chemotherapy or radiation therapy in a patient.

15. The combination of claim 14, wherein the package is a spray bottle, said spray bottle configured to administer the edible composition through a nozzle of the spray bottle.

16. The combination of claim 14, wherein the edible composition is at least partially frozen prior to administering to a patient.

17. The composition of claim 8, wherein the mixture of at least two edible oils consists of 0.01-49% olive oil, 10-85% coconut oil and 15-90% canola oil by weight relative to the total weight of the composition.

18. The composition of claim 8, wherein the composition is an emulsion.

19. The composition of claim 17, wherein the composition is an emulsion.

20. The composition of claim 17 including water, sugar, xanthan gum and flavouring agents.

* * * * *